United States Patent [19]

Nohara et al.

[11] Patent Number: 4,727,150
[45] Date of Patent: Feb. 23, 1988

[54] PYRIDYL METHYLSULFINYL BENZIMIDAZOLE DERIVATIVES

[75] Inventors: Akira Nohara; Yoshitaka Maki, both of Kyoto, Japan

[73] Assignee: Takeda Chemical Industries, Ltd., Osaka, Japan

[21] Appl. No.: 16,951

[22] Filed: Feb. 20, 1987

Related U.S. Application Data

[63] Continuation of Ser. No. 760,567, Jul. 29, 1985, abandoned.

[30] Foreign Application Priority Data

Aug. 16, 1984 [JP] Japan .................. 59-171070

[51] Int. Cl.$^4$ .......................... C07D 401/12
[52] U.S. Cl. ........................................ 546/271
[58] Field of Search ........................ 546/271

[56] References Cited

U.S. PATENT DOCUMENTS

| | | | |
|---|---|---|---|
| 4,045,563 | 8/1977 | Berntsson et al. | 546/271 |
| 4,255,431 | 3/1981 | Junggren et al. | 546/271 |
| 4,472,409 | 9/1984 | Jenn-Bilfinger | 546/271 |
| 4,575,554 | 3/1986 | Sih | 546/271 |

FOREIGN PATENT DOCUMENTS

| | | |
|---|---|---|
| 5129 | 10/1979 | European Pat. Off. |
| 74341 | 3/1981 | European Pat. Off. |
| 45200 | 2/1982 | European Pat. Off. |
| 2134523A | 8/1984 | United Kingdom |

Primary Examiner—Jane T. Fan
Attorney, Agent, or Firm—Wegner & Bretschneider

[57] ABSTRACT

The compound of the formula

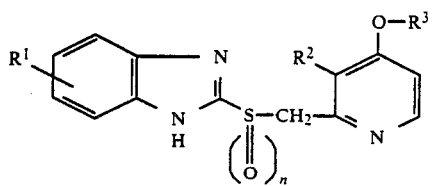

wherein $R^1$ is hydrogen, fluorine, methoxy or trifluoromethyl, $R^2$ is hydrogen or methyl, $R^3$ is a $C_{3-8}$ straight-chain or branched alkyl, and n denotes 0 or 1, or their pharmacologically acceptable salts is novel and useful for prophylaxis and therapy of digestive ulcers (e.g. gastric ulcer, duodenal ulcer) and gastritis.

9 Claims, No Drawings

PYRIDYL METHYLSULFINYL BENZIMIDAZOLE DERIVATIVES

This application is a continuation of U.S. application Ser. No. 760,567, filed July 29, 1985, now abandoned.

This invention relates to Benzimidazole derivatives useful as e.g. anti-ulcer agents and to a method of preparing them.

As the benzimidazole derivatives having anti-ulcer activity, those disclosed in e.g. U.S. Pat. No. 4,255,431 (Japanese Unexamined Patent Laid-open No. 141783/79) and U.S. Pat. No. 4,472,409 (Japanese Unexamined Patent Laid-open No. 135881/83) have been known.

However, while these known compounds have an acid-secretion-inhibiting action, their gastric mucous membrane protecting action is insufficient, thus being hardly considered satisfactory as anti-ulcer agents. Besides, these compounds are possessed of such drawbacks in the physico-chemical properties as being unstable and readily decomposed.

It is considered that gastrointestinal ulcer is induced by unbalance between aggressive factors, e.g. hydrochloric acid and pepsin, and defensive factors, e.g. mucus secretion and mucosal blood flow. Therefore, a medicine having both an action of inhibiting gastric acid secretion and an action of enhancing protection of gastric mucosa has been desired.

The present inventors diligently studied with the purpose of preparing an anti-ulcer agent having excellent actions of inhibiting gastric acid secretion, of protecting gastric mucosa and of antagonizing ulceration. They found that a certain type of benzimidazole derivatives meets the said purpose, and they conducted further study to accomplish the present invention.

The present invention relates to (1) benzimidazole derivatives of the formula (I)

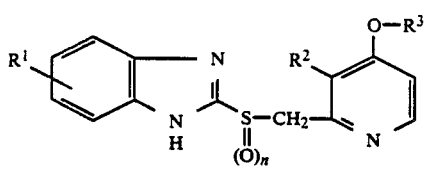

wherein $R^1$ is hydrogen, fluorine, methoxy or trifluoromethyl, $R^2$ is hydrogen or methyl, $R^3$ is a $C_{3-8}$ straight-chain or branched alkyl, and n denotes 0 or 1 or their pharmacologically acceptable salts and (2) a method for preparing a compound (I) or a salt thereof, which comprises allowing a compound of the formula (II)

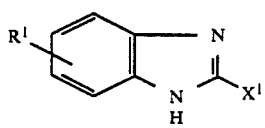

wherein $R^1$ is of the same meaning as defined above, to react with a compound of the formula (III)

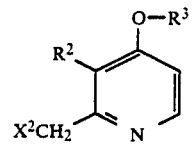

wherein $R^2$ and $R^3$ are of the same meaning as defined above, and one of $X^1$ and $X^2$ is SH and the other is a leaving group, and, when necessary, by subjecting the reaction product to oxidation.

In the above formulae, $C_{3-8}$ straight-chain or branched alkyl groups shown by $R^3$ are exemplified by n-propyl, iso-propyl, n-butyl, iso-butyl, n-pentyl, n-hexyl or n-octyl.

Examples of the leaving groups $X^1$ and $X^2$ in the above formulae are halogen, preferably chlorine, bromine or iodine, or a reactive esterified hydroxy group, e.g. an arylsulfonyloxy, for example, benzenesulfonyloxy or tosyloxy, or a $C_{1-4}$ alkylsulfonyloxy, for example, methanesulfonyloxy, or organic phosphoryloxy, for example, diphenylphosphoryloxy dibenzylphosphoryloxy or di-$C_{1-4}$alkylphosphoryloxy and the like.

$R^1$ may be located at 4- or 5-position, and preferably at 5-position.

A sulfide derivative (I) (n=0), among the object compounds of this invention, can be prepared by allowing a compound (II) to react with a compound (III). It is convenient to conduct this reaction in the presence of a base. The base is exemplified by alkali metal hydride e.g. sodium hydride and potassium hydride; alkali metal e.g. metallic sodium; sodium alcoholate e.g. sodium methoxide and sodium ethoxide; alkali metal carbonate e.g. potassium carbonate and sodium carbonate; and organic amines e.g. triethylamine. The solvent used for the reaction is exemplified by alcohols e.g. methanol and ethanol, as well as dimethylformamide. The amount of a base used for the reaction is usually in a little excess to the equivalent, but it may be in a large excess. Specifically, it is about 1–10 equivalents, more preferably about 1–4 equivalents. The reaction temperature ranges usually from about 0° C. to about the boiling point of the solvent then used, more preferably from about 20° C. to about 80° C. The reaction time ranges from about 0.2 to about 24 hours, more preferably from about 0.5 to about 2 hours.

A sulfinyl derivative (I) (n=1), which is also among the object compounds of this invention, can be prepared by subjecting a compound (I) (n=0) to oxidation. The oxidizing agent to be employed here is exemplified by peracid e.g. m-chloroperbenzoic acid, peracetic acid, trifluoroperacetic acid and permaleic acid, or sodium bromite or sodium hypochlorite or hydrogen peroxide. The solvent used for the reaction is exemplified by halogenated hydrocarbon e.g. chloroform and dichloromethane, ethers e.g. tetrahydrofuran and dioxane, amides e.g. dimethylformamide, alcohols, e.g. methanol, ethanol, propanol, and t-butanol or water, and these solvents may be used singly or in admixture. The oxidizing agent is used preferably in approximately equivalent or a little excess amount relative to the compound (I) (n=0). Specifically, it is about 1 to about 3 equivalents, more preferably about 1–1.5 equivalent. The reaction temperature ranges from that under ice-cooling to about the boiling point of the solvent then employed, usually from that under ice-cooling to room temperature, more preferably from about 0° C. to about 10° C. The reaction time usually ranges from about 0.1 to about 24 hours, more preferably from about 0.1 to about 4 hours.

The object compound (I) produced by the above reaction can be isolated and purified by conventional means e.g. recrystallization and chromatography.

The compound (I) of this invention may be led to pharmacologically acceptable salts thereof by per se conventional means, the salts being exemplified by hydrochloride, hydrobromide, hydroiodide, phosphate, nitrate, sulfate, acetate and citrate.

Among the compounds (I), those of n=0 give stable salts, while those of n=1 may exist as an aqueous solution though unstable.

The process of preparing the starting material (III) is described as follows.

Process 1)

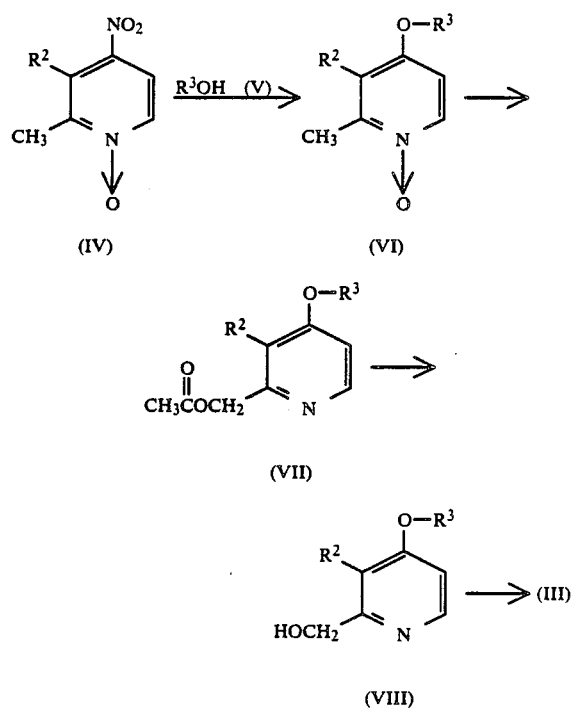

A nitro compound of the formula (IV) [wherein $R^2$ is of the same meaning as defined above] is allowed to react with an alcohol derivative $R^3OH$ (V) [wherein $R^3$ is of the same meaning as defined above] in the presence of a base to give an alkoxy derivative of the formula (VI) [wherein $R^2$ and $R^3$ are of the same meaning as defined above]. The base is exemplified by alkali metal e.g. lithium, sodium and potassium; alkali metal hydride e.g. sodium hydride and potassium hydride; alcoholate e.g. potassium t-butoxide and sodium propoxide; alkali metal carbonate or hydrogen carbonate e.g. potassium carbonate, lithium carbonate, sodium carbonate, potassium hydrogen carbonate and sodium hydrogen carbonate; or alkali hydroxide e.g. sodium hydroxide and potassium hydroxide. The solvent used for the reaction is exemplified by, besides $R^3OH$ itself, ethers such as tetrahydrofuran and dioxane as well as ketones such as acetone and methyl ethyl ketone, and further by acetonitrile, dimethylformamide and hexamethylphosphoric acid triamine. The reaction temperature is suitably selected within the range from those under ice-cooling to those near the boiling point of the solvent used. The reaction time ranges usually from about 1 to about 48 hours.

The thus-obtained compound (VI) is subjected to heating (about 80° to about 120° C.) in the presence of acetic anhydride singly or together with a mineral acid e.g. sulfuric acid and perchloric acid to give a 2-acetoxymethylpyridine derivative of the formula (VII) [wherein $R^2$ and $R^3$ are of the same meaning as defined above]. The reaction time ranges usually from about 0.1 to about 10 hours.

Then, the compound (VII) is subjected to alkalihydrolysis to give a 2-hydroxymethyl pyridine derivative of the formula (VIII) [wherein $R^2$ and $R^3$ are of the same meaning as defined above]. The alkali is exemplified by sodium hydroxide, potassium hydroxide, potassium carbonate and sodium carbonate. The solvent used for the reaction is exemplified by methanol, ethanol and water. The reaction temperature ranges usually from about 20° C. to about 60° C. The reaction time is within the range of from about 0.1 to about 2 hours.

The compound (VIII) is further subjected to reaction with a chlorinating agent such as thionyl chloride, or an esterifying agent, e.g. an organic sulfonic acid chloride such as methanesulfonyl chloride or p-toluenesulfonyl chloride, or an organic phosphoric acid chloride such as diphenylphosphoryl chloride to give the compound (III). The amount of the chlorinating agent used for the reaction is usually in equivalent to a large excess relative to the compound (VIII). The solvent used for the reaction is exemplified by chloroform, dichloromethane and tetrachloroethane. The reaction temperature is usually within the range of from about 20° C. to about 80° C., and the reaction time is about 0.1 to about 2 hours.

The amount of the organic sulfonic acid chloride or organic phosphoric acid chloride used for the reaction is usually in equivalent to a little excess, and the reaction is usually conducted in the presence of a base. The base is exemplified by organic base e.g., triethylamine and tributylamine, or inorganic base e.g. sodium carbonate, potassium carbonate and sodium hydrogen carbonate. The amount of a base used for the reaction is usually in equivalent to a little excess. The solvent used for the reaction is exemplified by chloroform, dichloromethane, carbon tetrachloride or acetonitrile. The reaction temperature ranges usually from that under ice-cooling to about the boiling point of the solvent then used. The reaction time ranges usually from a few minutes to a few hours. It is usually preferable to use the thus-produced compound (III) immediately for the reaction with a compound (II).

Process 2)

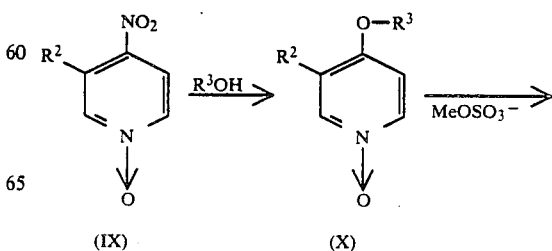

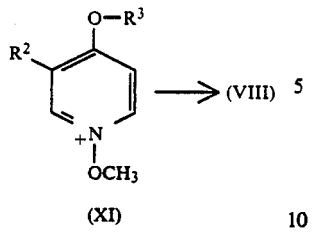

(XI)

By a reaction similar to the above-described process (1), a compound of the formula (IX) [wherein $R^2$ is of the same meaning as defined above] is led to a compound of the formula (X) [wherein $R^2$ and $R^3$ are of the same meaning as defined above].

Then, the compound (X) is subjected to methylation with dimethyl sulfate to give a compound of the formula (XI) [wherein $R^2$ and $R^3$ are of the same meaning as defined above]. The reaction can be conducted usually without solvent. The reaction temperature ranges from about 100° C. to about 120° C., and the reaction time is within the range of from about 0.1 to about 4 hours.

Further, the compound (XI) is allowed to react with a radical source such as ammonium persulfate or any other persulfate in methanol to give the above-mentioned compound (VIII). The reaction temperature is within the range of from about 20° C. to about 80° C., and the reaction time ranges from about 0.5 to about 4 hours.

Pharmacological actions of the compounds of the present invention are described as follows.

While the role of acid in causing gastric and duodenal ulcerations has been well known, importance of the protecting ability of gastric mucosa has been attracting the attention in recent years.

Miller T. A., Am. J. Physiol., 245, G601 (1983)

As a method of determining the protecting ability of gastric mucosa, gastric mocosal injury induced by ethanol [Robert A., Gastroenterology 77, 761 (1979)] is often used. This method was applied to evaluation of the compounds of this invention.

Experimental Method

Male Sprague-Dawley rats of 7-weeks old were fasted for 24 hours. These animals were administered test compounds into stomach by using a gastric tube. After 30 minutes, 1 ml of 100% ethanol was administered orally. The animals were killed by carbon dioxide gas 60 minutes after ethanol administration. The stomach was removed together with the lower part of esophagus and the duodenum. The esophagus was clipped, 10 ml of 1% formalin solution was instilled into the stomach from the duodenum, and then the duodenum was clipped. The whole stomach was immersed in 1% formalin solution. About 15 minutes later, the stomachs were opened along the greater curvature. The length of the lesions which occurred in the gastric antral mucosa was measured under a dissecting microscope with a square-grid eye piece (×10). The sum total length of the individual lesions in each animal was measured, and the average value per group was calculated. Based on the difference between the average value of each group and that of the control group, the inhibition rate was determined. The test compound was suspended in a 5% gum arabic solution, and administered in a volume of 2 ml/kg.

Experimental Results

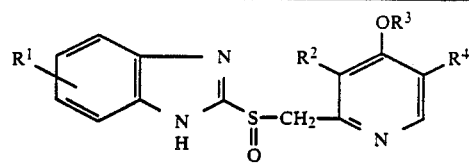

| $R^1$ | $R^2$ | $R^3$ | $R^4$ | Action of protecting gastric mucosa[a] $ID_{50}$ (mg/kg, p.o.) |
|---|---|---|---|---|
| H | H | $(CH_2)_2CH_3$ | H | 7.2 |
| H | $CH_3$ | $(CH_2)_2CH_3$ | H | 12.5 |
| H | H | $CH(CH_3)_2$ | H | 1.3 |
| 5-F | H | $CH(CH_3)_2$ | H | 8.8 |
| 5-$CF_3$ | H | $CH(CH_3)_2$ | H | 5.8 |
| H | H | $(CH_2)_3CH_3$ | H | 9.8 |
| H | H | $(CH_2)_5CH_3$ | H | 1.6 |
| H | H | $(CH_2)_7CH_3$ | H | 1.6 |
| 5-$OCH_3$ | $CH_3$ | $CH_3$ | $CH_3$*[1] | 22.0 |
| 5-$CF_3$ | $CH_3$ | $CH_3$ | H*[2] | 24.0 |

*[1] The compound disclosed in Example 23 of U.S. Pat. No. 4,255,431 (Japanese Unexamined Patent Laid-open No. 141783/1979)
*[2] The compound disclosed in Example 3 of U.S. Pat. No. 4,472,409 (Japanese Unexamined Patent Laid-open No. 135881/1983)
[a] Using 6 rats per group, each of the test compounds was administered in a dose of 1, 3, 10 and 30 mg/kg to determine $ID_{50}$.

As shown by the above data, the compounds of this invention have an evidently superior action of protecting gastric mucosa as compared with known compounds. Besides, the compound (I) of this invention shows excellent actions of inhibiting gastric acid secretion, protecting gastric mucous membrane and preventing ulceration.

Regarding the toxicity of the compound (I) of this invention, oral administration of the compound employed to test the action protecting gastric mucous membrane (compound of $R^1=H$, $R^2=H$, $R^3=(CH_2)_2CH_3$) in mice even in a dose of 500 mg/kg caused no fatal effect; thus the compound (I) generally is low in toxicity.

As described in the foregoing, the compound (I) of this invention has an anti-ulcer action, a gastric acid secretion controlling action and a mucous membrane protecting action, furthermore is of low toxicity and is relatively stable as a chemical substance. The compound (I) of this invention can thus be used for prophylaxis and therapy of digestive ulcers (e.g. gastric ulcer, duodenal ulcer) and gastritis in mammalian animals (e.g. mouse, rat, rabbit, dog, cat and man).

When the compound (I) of this invention is used as an anti-ulcer agent for the therapy of digestive ulcers in mammalian animals, it can be administered orally in a dosage form of capsules, tablets, granules, etc. by formulating with a pharmacologically acceptable carrier, excipient, diluent, etc. The dose is about 0.01–30 mg/kg/day, more preferably about 0.1–3 mg/kg/day.

Incidentally, the compound of this invention (I) (n=0) is useful as a starting material for preparing the compound (I) (n=1).

The processes of producing the starting compounds to be employed in the method of this invention as well as those of producing the compound (I) of this invention are specifically explained by the following Reference Examples and Working Examples.

REFERENCE EXAMPLE 1

To a solution of sodium n-propoxide solution prepared by dissolving sodium (1.7 g) in n-propanol (200 ml) was added to a hot solution of 2-methyl-4-nitropyridine-1-oxide (5.2 g) in n-propanol (210 ml). The mixture was stirred for ten minutes, then n-propanol was evaporated off. To the residue was added chloroform under ice-cooling, and insoluble materials were removed by means of celite filtration. From the resultant solution was removed chloroform by evaporation. The residue was subjected to a silica-gel column chromatography, followed by elution with 10% methanol-chloroform to yield 2-methyl-4-propoxypyridine-1-oxide (4.7 g) as an oily substance.

By this process, compounds (VI) were prepared from compounds (IV).

| Compound (VI) | | |
|---|---|---|
| $R^2$ | $R^3$ | State |
| H | $(CH_2)_3CH_3$ | Oily |
| H | $(CH_2)_5CH_3$ | Oily |
| H | $(CH_2)_7CH_3$ | Oily |
| H | $CH(CH_3)_2$ | Oily |

REFERENCE EXAMPLE 2

In n-propanol (42 ml) was dissolved 2,3-dimethyl-4-nitropyridine-1-oxide (841 mg). To the solution was added anhydrous potassium carbonate (2.1 g), and the mixture was stirred at 80° C. for 22 hours, followed by filtration with celite. The filtrate was concentrated, and the residue was chromatographed on a column of silica-gel (50 g), which was eluted with 5% methanol-chloroform to yield 2,3-dimethyl-4-propoxypyridine-1-oxide (360 mg) as an oily substance.

NMR spectrum (CDCl$_3$)δ: 1.07 (3H, t, J=7.5 Hz), 1.65–2.02 (2H, m), 2.21 (3H, s), 2.52 (3H, s), 3.99 (2H, t, J=6 Hz), 6.68 (1H, d, J=6 Hz), 8.15 (1H, d, J=6 Hz)

REFERENCE EXAMPLE 3

A mixture of 2-methyl-4-propoxypyridine-1-oxide (8.6 g), acetic anhydride (8.6 ml) and concentrated sulfuric acid (two drops) was heated at 100° C. for five minutes, to which were added ice-water and an excess amount of sodium carbonate. The mixture was subjected to extraction with chloroform. The extract was dried with sodium sulfate, and the solvent was evaporated off. The residue was chromatographed on a column of silica-gel (200 g), which was eluted with carbon tetrachloride-acetone (5:3). The eluate was subjected to evaporation to remove the solvent. The residue (7.3 g) was dissolved in a solution of potassium hydroxide (2.8 g) in a mixture of water (3 ml) and methanol (60 ml). The resultant solution was stirred at room temperature for 15 minutes, to which were added ice-water and an excess amount of sodium carbonate. The mixture was subjected to extraction with ethyl acetate. The extract was dried with sodium sulfate, then the solvent was evaporated off. The residue was chromatographed on a column of silica-gel (150 g), which was eluted with 5% methanol-chloroform to yield 2-hydroxymethyl-4-propoxypyridine (4.4 g) as an oily substance.

NMR spectrum (CDCl$_3$)δ: 1.0 (3H, t, J=7.5 Hz), 1.79 (2H, m), 3.92 (2H, t, J=6 Hz), 4.51–4.90 (1H, br), 4.68 (2H, s), 6.68 (1H, dd, J=2 and 6 Hz), 6.80 (1H, d, J=2 Hz), 8.28 (1H, d, J=6 Hz)

By this process, compounds (VIII) were prepared from compounds (VI).

| Compound (VIII) | | |
|---|---|---|
| $R^2$ | $R^3$ | State |
| $CH_3$ | $CH_2CH_2CH_3$ | Oily |
| H | $(CH_2)_3CH_3$ | Oily |
| H | $(CH_2)_5CH_3$ | Oily |
| H | $(CH_2)_7CH_3$ | Oily |
| H | $CH(CH_3)_2$ | Oily |

EXAMPLE 1

To a solution of 2-hydroxymethyl-3-methyl-4-propoxypyridine (680 mg) dissolved in chloroform (35 ml) was added thionyl chloride (1.1 ml). The mixture was refluxed for 30 minutes, which was then concentrated. The residue was dissolved in methanol (10 ml). The solution was added dropwise to a mixture of 2-mercaptobenzimidazole (536 mg), 28% sodium methoxide solution (4.5 ml) and methanol (20 ml), which was refluxed for 30 minutes. From the resultant mixture methanol was removed by evaporation. To the residue were added ice and an excess amount of sodium carbonate, which was subjected to extraction with ethyl acetate. The extract was dried with sodium sulfate and the solvent was removed by evaporation to yield 2-(3-methyl-4-propoxy-2-pyridyl)methylthiobenzimidazole (1.1 g) as an oily substance.

NMR spectrum (CDCl$_3$)δ: 0.98 (3H, t, J=7.5 Hz), 1.54–1.92 (2H, m), 2.15 (3H, s), 3.80 (2H, t, J=6 Hz), 4.43 (2H, s), 6.55 (1H, d, J=6 Hz), 7.09 (2H, m), 7.50 (2H, m), 8.21 (1H, d, J=6 Hz)

By this process, compounds (I) (n=0) were prepared from compounds (II) and compounds (III).

| Compound (I) (n = 0) | | | |
|---|---|---|---|
| $R^1$ | $R^2$ | $R^3$ | m.p. (°C.) |
| H | H | $(CH_2)_2CH_3$ | 84–86 |
| H | H | $(CH_2)_3CH_3$ | Oily*$^1$ |
| H | H | $(CH_2)_5CH_3$ | 64–65 |
| H | H | $(CH_2)_7CH_3$ | 75–76 |
| H | H | $CH(CH_3)_2$ | 140–140.5 |
| 5-$CF_3$ | H | $(CH_2)_7CH_3$ | 93–94.5 |
| 5-$CF_3$ | H | $CH(CH_3)_2$ | 131–132 |
| 5-F | H | $CH(CH_3)_2$ | 133–134 |
| 5-$OCH_3$ | H | $(CH_2)_3CH_3$ | Oily*$^2$ |
| 5-$OCH_3$ | H | $(CH_2)_5CH_3$ | Oily*$^3$ |

*$^1$NMR spectrum (CDCl$_3$)δ: 0.95(3H,t,J=7.5HZ), 1.16–1.90(4H,m), 3.95(2H,t,J=6Hz),4.31(2H,s),6.70(1H,d,d,J=3 and 6Hz),6.85(1H,d,J=3Hz), 7.10–7.27(2H,m), 7.43–7.63(2H,m), 8.35(1H,d,J=6Hz)
*$^2$NMR spectrum (CDCl$_3$)δ: 0.94(3H,t,J=7.5Hz), 1.28–1.90 (4H,m), 3.81(3H,s), 3.98(2H,t,J=6Hz), 4.29(2H,s), 6.63–6.90(3H,m), 7.05(1H,d,J=3Hz), 7.43(1H,d,J=9Hz), 8.40 (1H,d,J=6Hz)
*$^3$NMR spectrum (CDCl$_3$)δ: 0.9(3H,t,J=6Hz), 1.10–1.50(6H,m), 1.74(2H,m), 3.75(3H,s), 3.90(2H,t,J=6Hz), 4.29(2H,s), 6.60–6.88(3H,m), 7.00(1H,d,J=2Hz), 7.41(1H,d,J=9Hz), 8.36(1H,d,J=6Hz)

EXAMPLE 2

To a solution of 2-(3-methyl-4-propoxy-2-pyridyl)-methylthiobenzimidazole (1 g) in chloroform (20 ml) was added dropwise over 10 minutes under ice-cooling m-chloroperbenzoic acid (750 mg) dissolved in chloroform (10 ml). The solution was chromatographed directly on a column of silica gel (50 g), which was eluted with ethyl acetatehexane (1:1) and then with 5% methanol-ethyl acetate. From the eluate was removed the solvent. The residue was recrystallized from acetone-ether-hexane to give 415 mg of 2-[3-methyl-4-propoxy- 2-pyridyl)methylsulfinylbenzimidazole.4/5H$_2$O as crystals, m.p. 81°–83° C.

By this process, compound (I) (n=1) were prepared from compounds (I) (n=0)

| Compound (I) (n = 1) | | | |
|---|---|---|---|
| R$^1$ | R$^2$ | R$^3$ | m.p. (°C.) |
| H | H | (CH$_2$)$_2$CH$_3$ | 123–125(d) |
| H | H | (CH$_2$)$_3$CH$_3$ | 119–120(d) |
| H | H | (CH$_2$)$_5$CH$_3$ | 127–128 |
| H | H | (CH$_2$)$_7$CH$_3$ | 101–102.5 |
| *H | H | CH(CH$_3$)$_2$ | 131–133(d) |
| 5-CF$_3$ | H | —(CH$_2$)$_7$CH$_3$ | 122.5–124.0(d) |
| 5-CF$_3$ | H | —CH(CH$_3$)$_2$ | 146–155(d) |
| 5-F | H | —CH(CH$_3$)$_2$ | 145–147(d) |
| 5-OCH$_3$ | H | (CH$_2$)$_3$CH$_3$ | 112–113(d) |
| 5-OCH$_3$ | H | (CH$_2$)$_5$CH$_3$ | 99–101(d) |

*) acetone (crystallization solvent)
(Note) (d): decomposition

What we claim is:

1. A compound of the formula

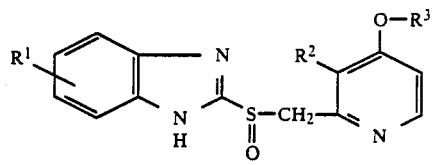

wherein R$^1$ is hydrogen, R$^2$ is hydrogen and R$^3$ is isopropyl or a C$_{6-8}$ straight-chain or branched alkyl, or a pharmacologically acceptable salt thereof.

2. A compound according to claim 1, wherein R$^3$ is isopropyl.

3. A compound according to claim 1, wherein R$^3$ is a C$_{6-8}$ straight-chain alkyl.

4. A compound according to claim 1, wherein R$^3$ is a C$_{6-8}$ branched alkyl.

5. A compound according to claim 1, wherein R$^3$ is hexyl.

6. A compound according to claim 1, wherein R$^3$ is octyl.

7. A compound according of claim 1, wherein the compound is 2-(4-hexyloxy-2-pyridyl)methylsulfinylbenzimidazole.

8. A compound according to claim 1, wherein the compound is 2-(4-octyloxy-2-pyridyl)methylsulfinylbenzimidazole.

9. A compound according to claim 1, wherein the compound is 2-(4-isopropoxy-2-pyridyl)methylsulfinylbenzimidazole.

* * * * *